United States Patent
Oluseyi et al.

(10) Patent No.: US 6,603,538 B1
(45) Date of Patent: Aug. 5, 2003

(54) METHOD AND APPARATUS EMPLOYING OPTICAL EMISSION SPECTROSCOPY TO DETECT A FAULT IN PROCESS CONDITIONS OF A SEMICONDUCTOR PROCESSING SYSTEM

(75) Inventors: Hakeem Oluseyi, Stanford, CA (US); Moshe Sarfaty, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/721,403

(22) Filed: Nov. 21, 2000

(51) Int. Cl.$^7$ .................. G01N 21/62; H01L 21/00; H01L 21/66

(52) U.S. Cl. ............... 356/72; 356/316; 216/60

(58) Field of Search ............... 356/72, 316; 216/60; 438/16; 427/8; 118/712

(56) References Cited

U.S. PATENT DOCUMENTS

| | | | |
|---|---|---|---|
| 4,208,240 A | 6/1980 | Latos | |
| 4,707,611 A | 11/1987 | Southwell | |
| 4,776,695 A | 10/1988 | van Pham et al. | |

(List continued on next page.)

FOREIGN PATENT DOCUMENTS

| | | |
|---|---|---|
| EP | 0677737 | 10/1995 |
| EP | 0756318 | 1/1997 |
| EP | 0768701 | 4/1997 |
| EP | 0878842 | 11/1998 |
| JP | 05291188 | 5/1993 |
| JP | 10335309 | 12/1998 |

OTHER PUBLICATIONS

White et al., "Spatial Characterization of Wafer State Using Principal Component Analysis of Optical Emission Spectra in Plasma Etch, IEEE Transactions on Semiconductor Manufacturing", IEEE Inc., New York, US, vol. 10, No. 1, Feb. 1997, p. 52–61, XP002924118, ISSN: 0894–6507.

Primary Examiner—F. L. Evans
Assistant Examiner—Kara Geisel
(74) Attorney, Agent, or Firm—Ken Brooks; Joseph Bach

(57) ABSTRACT

A method and an apparatus system feature detecting faults in process conditions of a plasma-based semiconductor processing system by sensing the spectral emissions of the plasma. As a result, the method includes sensing optical energy produced by the plasma and identifying the fault in the process conditions as a function of one or more of the plurality of spectral bands. To that end, the apparatus includes a detector in optical communication with the processing chamber to sense optical energy generated by the plasma, and a spectrum analyzer, in electrical communication with the optical detector. The spectrum analyzer resolves the spectral bands and produces information corresponding thereto. A processor is in electrical communication with the spectrum analyzer, and a memory is in electrical communication with the processor. The memory includes a computer-readable medium having a computer-readable program embodied therein that controls the system to carry-out the method.

21 Claims, 10 Drawing Sheets

U.S. PATENT DOCUMENTS

| | | | |
|---|---|---|---|
| 5,048,960 A | 9/1991 | Hayashi et al. | |
| 5,160,402 A | 11/1992 | Cheng | |
| 5,270,222 A | 12/1993 | Moslehi | |
| 5,335,066 A | 8/1994 | Yamada et al. | |
| 5,374,327 A | 12/1994 | Imahashi et al. | |
| 5,386,119 A | 1/1995 | Ledger | |
| 5,403,433 A | 4/1995 | Morrison et al. | |
| 5,493,401 A | 2/1996 | Horie et al. | |
| 5,565,114 A | 10/1996 | Saito et al. | |
| 5,643,364 A | 7/1997 | Zhao et al. | |
| 5,658,423 A * | 8/1997 | Angell et al. | 204/192.13 |
| 5,686,993 A | 11/1997 | Kokubo et al. | |
| 5,694,207 A | 12/1997 | Hung et al. | |
| 5,711,843 A | 1/1998 | Jahns | |
| 5,719,495 A | 2/1998 | Moslehi | |
| 5,877,032 A | 3/1999 | Guinn et al. | |
| 5,885,472 A | 3/1999 | Miyazaki et al. | |
| 5,983,906 A | 11/1999 | Zhao et al. | |
| 6,046,796 A * | 4/2000 | Markle et al. | 216/60 |
| 6,052,183 A | 4/2000 | Lee | |
| 6,068,783 A | 5/2000 | Szetsen | |
| 6,074,568 A | 6/2000 | Adachi et al. | |
| 6,153,115 A * | 11/2000 | Le et al. | 216/60 |
| 6,157,867 A * | 12/2000 | Hwang et al. | 216/60 |
| 6,278,519 B1 | 8/2001 | Rosencwaig et al. | |
| 6,278,809 B1 | 8/2001 | Johnson et al. | |
| 6,297,880 B1 | 10/2001 | Rosencwaig et al. | |
| 6,304,326 B1 | 10/2001 | Aspnes et al. | |

* cited by examiner

METHOD AND APPARATUS EMPLOYING OPTICAL EMISSION SPECTROSCOPY TO DETECT A FAULT IN PROCESS CONDITIONS OF A SEMICONDUCTOR PROCESSING SYSTEM

BACKGROUND OF THE INVENTION

The present invention relates to monitoring of semiconductor processes. More particularly, the present invention relates to a method and apparatus to detect a fault in process conditions of a plasma-based semiconductor processing system.

Process control and diagnostics are important to determine the characteristics of films being deposited during semiconductor processing. For example, current process control and diagnostics of plasma enhanced deposition processes involve three techniques: optical endpoint detection, interferometric endpoint detection and test wafer measurement technique. The optical endpoint detection technique involves ascertaining a process endpoint by monitoring one or two narrow bands of optical emission from process plasmas. A drawback with this technique concerns the limited information regarding the characteristics of the films being deposited.

The interferometric endpoint technique takes advantage of interferometry to determine whether a film has obtained a predetermined thickness. Drawbacks associated with the interferometric endpoint technique include the limitations of materials that are suitable for use with interferometric measurements. Some materials, such as metals, do not show interferometric interference fringes unless the material being measured is extremely thin. Secondly, the interferometric technique does not predict true process endpoints.

The test wafer measurement technique involves direct measurement of a film disposed on a substrate. As a result, the test wafer measurement technique evaluates the last process step performed by examination of test wafers that are processed within a group of production wafer. This is a drawback, because this technique does not identify failures of intermediate process steps. This may result in the loss of a great number of processed wafers. In addition, the test wafer measurement technique is destructive in nature, substantially reducing the operational life of the test wafer.

Recent advancements have been made in monitoring of semiconductor etch processes employing spectroscopic techniques. For example, in U.S. Pat. No. 6,068,783 to Szetsen, a spectroscopic method is disclosed for selecting a single plasma gas as a probe, in a cleaned plasma etch chamber; measuring the spectral intensities of the plasma gas; and plotting the measured spectral intensities either directly or indirectly against the RF time. In this manner, a single plasma gas is selected which exhibits opposite relationships with RF time at two respective wavelengths to facilitate in-situ monitoring of the etching process.

In U.S. Pat. No. 5,877,032 to Guinn et al. a process is disclosed in which a plasma containing a fluorocarbon gas is monitored using optical emission spectroscopy to effect control of an etch process. To control the process based on an observation of photoresist etch rate, two wavelengths are monitored. One wavelength is associated with a species, that is produced by the interaction between the photoresist and the plasma, and one wavelength is associated with a species related to the plasma intensity. The ratio of the optical intensity at these two wavelengths is determined in real time processing, and the ratio is associated with acceptable process conditions by referring to a predetermined calibration curve that associates a particular ratio with a particular photoresist etch rate for a given set of process conditions. Were the ratio observed not to be within a certain range of ratios determined to indicate acceptable process conditions, the plasma conditions are either changed to bring the ratio back within the desired range, or the process is stopped until the problem is corrected. To control the process based on an observation of contact hole etch rate, a wavelength associated with one species in the plasma is monitored at two different times during the etch process. A ratio of the measured intensity at these two different times is obtained. Calibration information is then used to determine if the ratio indicates that the process is proceeding acceptably. If the ratio is not within the acceptable range, remedial action is taken. However, the information obtained from the aforementioned spectroscopic techniques is limited in its ability to detect and classify faults that occur during the process.

What is needed, therefore, is a technique to detect and classify faults during processing of a substrate in a semiconductor process.

SUMMARY OF THE INVENTION

Provided are a method and an apparatus that feature detecting faults in process conditions of a plasma-based semiconductor processing system by sensing the spectral emissions of the plasma. The method includes sensing optical energy produced by the plasma and identifying the faulting the process conditions as a function of one or more of the plurality of spectral bands. Specifically, the optical energy has a plurality of spectral bands associated therewith, and a subset of the spectral bands includes information corresponding to one or more faults that may occur in the process conditions of the processing chamber. Examples of the process conditions which may cause faults include incorrect pressurization of the processing chamber, degradation of optical data paths, arcing between the substrate and an electrode, incorrect film being deposited on the substrate, the substrate not being properly situated on a pedestal and the like. Various techniques are employed to identifying the aforementioned faults from the subset of spectral bands, including identifying variations in the total intensity or identifying a ratio between multiple subsets of the spectral bands. In addition, detailed information that correlates the fault with the subsystem of the processing system that causes the same is achieved by analyzing the aforementioned subsets of spectral bands, as well as spectral bands containing information concerning the characteristics of a film being deposited. The apparatus includes a detector in optical communication with the processing chamber to sense optical energy generated by the plasma, and a spectrum analyzer, in electrical communication with the optical detector. The spectrum analyzer resolves the spectral bands and produces information corresponding thereto. A processor is in electrical communication with the spectrum analyzer, and a memory is in electrical communication with the processor. The memory includes a computer-readable medium having a computer-readable program embodied therein that controls the system to carry-out the method.

DETAILED DESCRIPTION OF THE INVENTION

Figure 1:
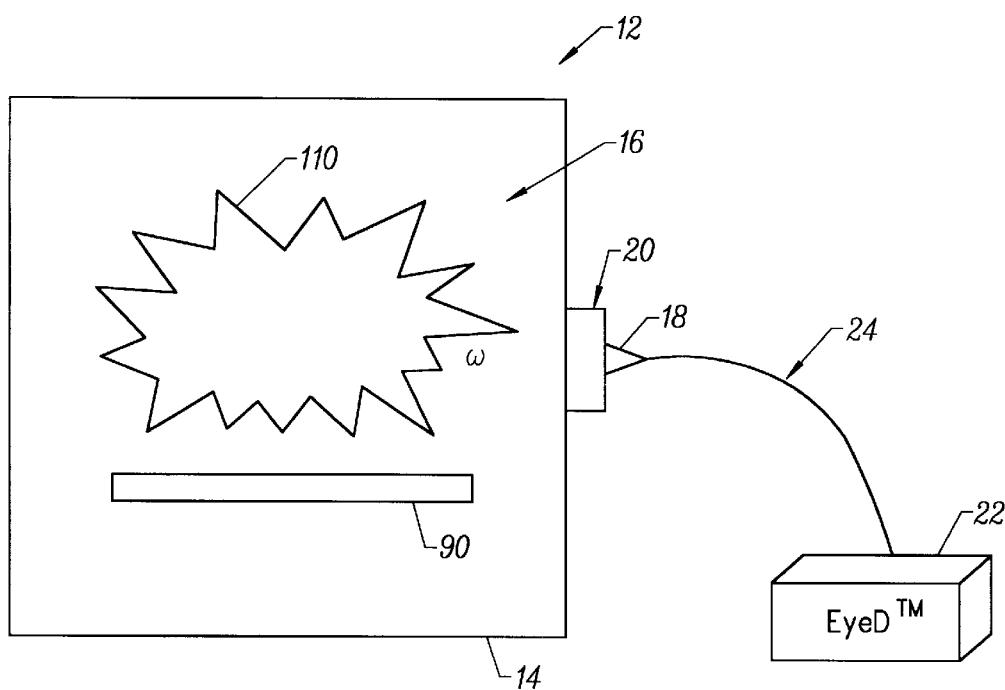
FIG. 1 is a simplified plan view of plasma-based semiconductor processing system in accordance with the present invention.

Referring to FIG. 1, a plasma-based semiconductor processing system 12 includes a housing 14 that defines a processing chamber 16. A sensor assembly 18 is in optical communication with the processing chamber 16 via a window 20 disposed in the housing 14. A spectrum analyzer 22 is in data communication with the sensor assembly 18 via a fiber-optic cable 24. The sensor assembly 18 may include any known detector in the art, such as a charged-coupled-device (CCD) and typically has a dispersive grating disposed between the CCD device and the window 20. In this manner, each of the pixels associated with the CCD device may correspond to a set of wavelengths that differs from the set of wavelengths that the remaining pixels of the CCD device are associated. An exemplary spectrum analyzer is sold under the trade name EyeD™ by Applied Material, Inc. of Santa Clara, Calif., the assignee of the rights in the present patent application. The system 12 may be any plasma-based system known in the semiconductor art, e.g., plasma etch system, sputter deposition system and the like, for purposes of the present discussion, the system 12 will be described as a plasma enhanced chemical vapor deposition (PECVD) system.

Figure 2:
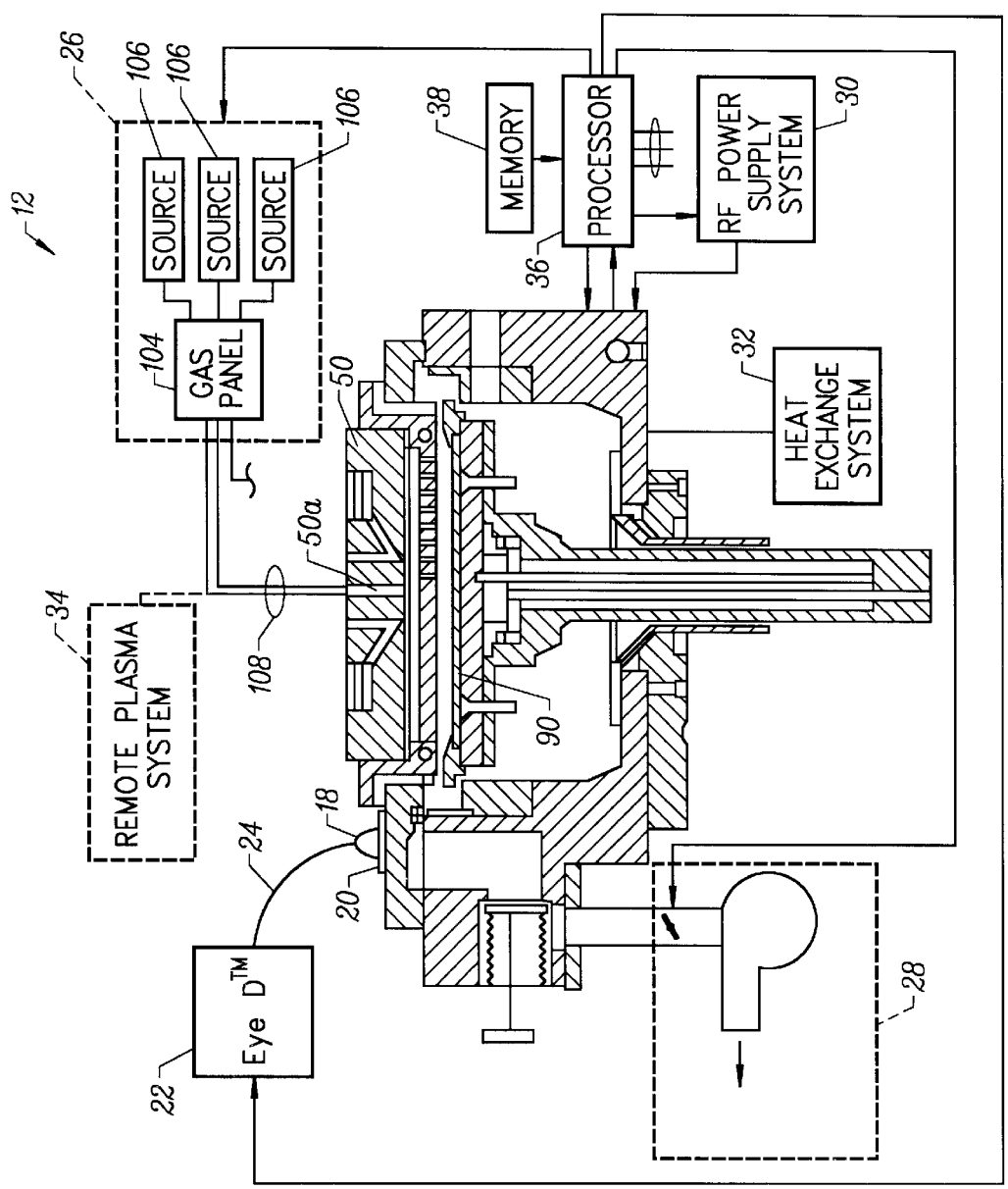
FIG. 2 is a detailed view of the semiconductor processing system, shown above in FIG. 1.

Referring to FIG. 2, the exemplary PECVD system 12 includes a gas delivery system 26, a vacuum system 28, an RF power supply system 30, a heat exchange system 32, and a remote plasma system 34 all operated under control of a processor 36. A memory 36, suitable for storing control programs, is in data communication with the processor 36. The gas delivery system 26, vacuum system 28, heat exchange system 32, and remote plasma system 34 are all in fluid communication with the processing chamber 16, discussed more fully below.

Figure 3:
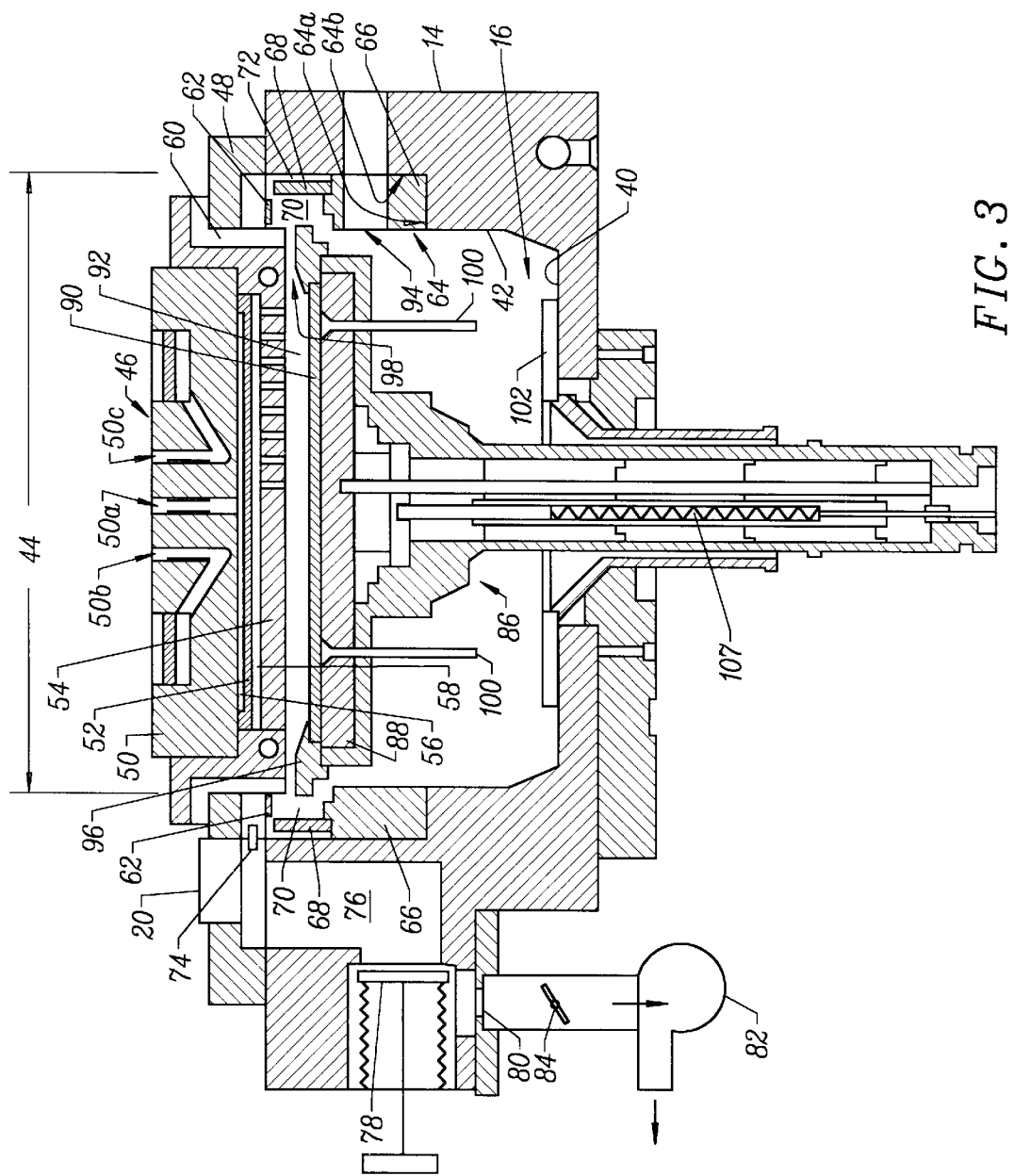
FIG. 3 is a detailed cross-sectional view of processing chamber, shown above in FIGS. 1 and 2.

Referring to FIG. 3, housing 14 includes a base wall 40 having a sidewall 42 extending therefrom and terminating in an opening 44. A lid 46 is moveably attached to the sidewall 42 to selectively seal the opening 44. The lid 46 includes a body 48 having a throughway in which a gas-feed cover plate 50, baffle plate 52 and a showerhead 54 are disposed. The gas-feed cover plate 50 includes a plurality of apertures, shown generally as 50a–c. One of the apertures, 50a, is centrally disposed and extends completely through the gas-feed cover plate 50 between the opposing surfaces thereof. The showerhead 54 is disposed adjacent to, and spaced-apart from, the gas-feed cover plate 50. The baffle plate 52 is disposed between the gas-feed cover plate 50 and the showerhead 54. The baffle plate 52 is spaced-apart from the gas-feed cover plate 50, defining a gap 56 therebetween. The showerhead 54 is spaced-apart from the baffle plate 52, defining a space 58 therebetween. Throughways in the baffle plate 52 place the gap 56 and the space 58 in fluid communication, and a plurality of apertures in the showerhead 54 place the space 58 in fluid communication with the processing chamber 16. Disposed between the showerhead 54 and the body 48 is an isolator 60. A ceramic liner 62 covers a portion of the body 48 that faces the processing chamber 16.

The sidewall 42 includes an annular recess 64 having a nadir surface 64a and a side surface 64b. A ceramic ring 66 is positioned within the annular 64 to completely cover the nadir surface 64a and extends upwardly toward the opening 44, partially covering the side surface 64b. A wall liner 68 is positioned in the annular recess 64 to cover the remaining segment of the side surface 64b located between the opening 44 and the ceramic ring 66. In this manner, an annular pumping channel 70 is defined between the ceramic liner 62, the ceramic ring 66, the wall liner 68 and the isolator 60. The annular pumping channel 70 is located proximate to the showerhead 54. The wall liner 68 is spaced-apart from both the side surface 64b and the wall liner 68 and forms a passageway 72 between the lid 46 and the wall liner 68.

In fluid communication with the annular pumping channel 70 is an exhaust aperture 74 to place the processing chamber 16 in fluid communication with a pumping plenum 76. A valve 78, in fluid communication with the pumping plenum 76, gates the exhaust into an exhaust vent 80 from the pumping plenum 76 that occurs under vacuum produced by a vacuum pump 82. The vacuum pump includes a throttle valve 84.

A pedestal 86, that may be resistively heated, is disposed within the processing chamber 16 and includes a pocket 88 adapted to receive a substrate 90, such as a semiconductor wafer. In this manner, the pedestal 86 supports the substrate 90 within the processing chamber 16. The pedestal 86 may be moved relative to the lid 46 and the base wall 40 to place the substrate 90 in a processing zone 92, disposed proximate to the showerhead 54, and a loading position where the pocket 88 is positioned below an access port 94 that is formed into the housing 14 and ceramic ring 66. The access port 94 can be hermetically-sealed to prevent the flow of process fluids from regressing from the processing chamber 16. The movement of the pedestal 86 may be achieved by employing a self-adjusting lift mechanism, described in detail in U.S. Pat. No. 5,951,776 to Selyutin et al., entitled "Self-Aligning Lift Mechanism", and assigned to the assignee of the present invention.

A ring 96 that may either be a clamp ring or a shadow ring, dependent upon the process, is positioned to contact a periphery of the pedestal 86 so as to surround the substrate 90 when placed in the processing zone 92. In this manner, an annular choke aperture 98 may be defined between the isolator 60 and ring 96. The ring 96 may be made of any suitable material depending upon the application, such as fused silica, titanium and the like. Were the ring 96 a shadow ring, the ring 96 is received on the ceramic ring 66 defining a space between the ring 96 and the pedestal 86, were the pedestal 86 in the loading position, i.e., retracted downwardly in the processing chamber 16. As the pedestal 86 supporting the next substrate is raised into processing position, it picks up the ring 96. The position of the substrate 90 is be maintained on the pedestal 86 via vacuum chucking the substrate 90 thereto.

Were the ring 96 a clamp ring, the ring 96 would securely fasten the substrate 90 to the pedestal 86 during processing. Thus, the ring 96 would securely position substrate 90 onto the pedestal 86 in addition to, or instead of, vacuum chucking the substrate 90 thereto.

Lift pins 100 are movably attached to the pedestal 86 so that one end of the same may engage a vertically movable lifting ring 102 positioned between the underside of the pedestal 86 and the base wall 40. The lift pins 100 extend beyond the surface of the pedestal 86 in which the substrate pocket 88 is formed when the lifting ring 102 is moved upwardly to engage the underside of the lift pins 100. Positioning of a substrate 90 with respect to the substrate pocket 88 is achieved via a robot blade (not shown) in cooperation with the lift pins 100 when the pedestal 86 is in the loading position. When the pedestal 86 is in the loading position, the substrate 90 is spaced-apart from the substrate pocket 88 allowing the robot blade access to the substrate 90. The substrate 90 is lifted from and placed onto the pedestal 86 by relative motion between the lift pins 100 and the pedestal 86. To receive the substrate 90 into the substrate pocket 88, the pedestal 86 rises toward the processing zone 92. A suitable robotic transfer assembly is described in U.S. Pat. No. 4,951,601 to Maydan and assigned to the assignee of the present invention.

Referring again to FIG. 2, the gas delivery system 26 includes gas supply panel 104 and a plurality of fluid sources, solid sources or combinations thereof, shown generally as gas source 106. The supply line for each of the process gases include a shut-off valve (not shown) that can be used to automatically or manually shut off the flow of process fluids, as well as a mass flow controller (not shown) that measures the flow of fluids through each of the supply lines. The rate at which the process and carrier fluids including, for example, silane ($SiH_4$), nitrous oxide ($N_2O$), argon (Ar), nitrogen ($N_2$), and/or other dopant or reactant sources, are supplied to processing chamber 16 is also controlled by temperature-based liquid or gas mass flow controllers (MFCs) (not shown) and/or by valves (not shown). In alternative embodiments, the rate at which the process and carrier fluids are supplied to the processing chamber 16 may be controlled by a pressure-based fixed, or variable, aperture. Were toxic fluid, such as, ozone ($O_3$), or halogenated gas, used in the process, the several shut-off valves may be positioned on each gas supply line in conventional configurations. Gas supply panel 104 has a mixing system that receives the deposition process and carrier fluids from the sources 106 for mixing and sending to an aperture 50a and a gas-feed cover plate 50 via supply lines 108. In the specific embodiment, the mixing system, the input manifold to the mixing system, and the output manifold from the mixing system to the aperture 50a may be made of nickel or of a material such as alumina plated with nickel.

Referring to both FIGS. 2 and 3, in operation the pedestal 86 places the substrate 90 in the process zone 92 and process fluids are received from the source 106 into the aperture 50a, through the gas-feed cover plate 50, the baffle plate 52, and the showerhead 54 to enter the processing zone 92. The process fluids flow radially outward across the edge of substrate 90 reacting with the exposed surface thereof to form a desired film. Thereafter, the fluid flow is deflected past the ring 96 and into pumping channel 70 via the choke aperture 98. Upon entering pumping channel 70, the exhaust gas is routed around the perimeter of the process chamber 16, to be evacuated by the vacuum pump 82.

Referring to FIGS. 1, 2 and 3 the process conditions are measured as a function of the spectral emission of the plasma present to detect any faults that may be present. Specifically, spectral bands are identified that contain information concerning faults in the process conditions. The spectral bands of interest were determined while analyzing spectra of films being deposited on multiple substrates. In one example, multiple substrates, each of which is approximately 300 mm in diameter, are analyzed during deposition of a silicon containing film thereon. The RF power supply system system 30 supplied a voltage to the showerhead 54 in the range of 283 to 437 Watts, and the pedestal 86 placed substrate 90 a predetermined distance from the showerhead 54 in the range of 475 to 550 mils. The chamber pressure was established by the vacuum system 28 to be in the range of 2.43 to 2.97 milliTorr. The gas delivery system 26 supplied silane, $SiH_4$, into the processing chamber 16 from one of the sources 106 at a rate in the range of 247–260 sccm. A flow of nitrous oxide, $N_2O$, was introduced from one of the sources 106 at a rate in the range of 3,325 to 3,850 sccm.

Specifically, the spectral response from the plasma 110 is analyzed for a set of substrates to have a film deposited thereon, with the aforementioned parameters being set at the center-point of the ranges provided. From this center-point, or baseline, spectra are observed. The spectra are then sensed for substrates 90 to have films deposited having faults introduced into the processing system 12. These spectra are referred to as fault spectra. The faults introduced include varying the aforementioned parameters from the center-point, thereby altering the process conditions, from the baseline process condition. Additional faults also include inappropriately positioning a substrate on a pedestal 86 and degradation of the optical subsystem, including clouding of the window 20 due to deposition of a film thereon. The fault spectra are compared to the baseline spectra. Specifically, the ranges of wavelength that demonstrate an intensity change, with respect to the intensity of the baseline spectra, are identified as containing information corresponding to the faults of interest, discussed more fully below.

The fault and baseline spectra sensed are in a range of wavelengths from 200 to 900 nm. The total intensity of these wavelengths is sensed employing a multi-channel CCD sensor assembly. In the present example, a CCD sensor has an array of 2048 pixels, each of which is associated with a differing band of wavelengths of spectral energy providing an average spectral resolution of 0.32 nm per pixel. In each pixel, the time averaged intensity of the wavelengths associated therewith is obtained. Specifically, the spectral energy is sensed six times a second, i.e., once every 163 ms referred to as integrated data. An average of the integrated data is obtained providing a data point. The data points obtained from each of the 2048 pixels is obtained and summed, providing summed data. Summed data is collected sixty times, which is then summed together, providing the total intensity of the wavelengths referred to above.

Figure 4:
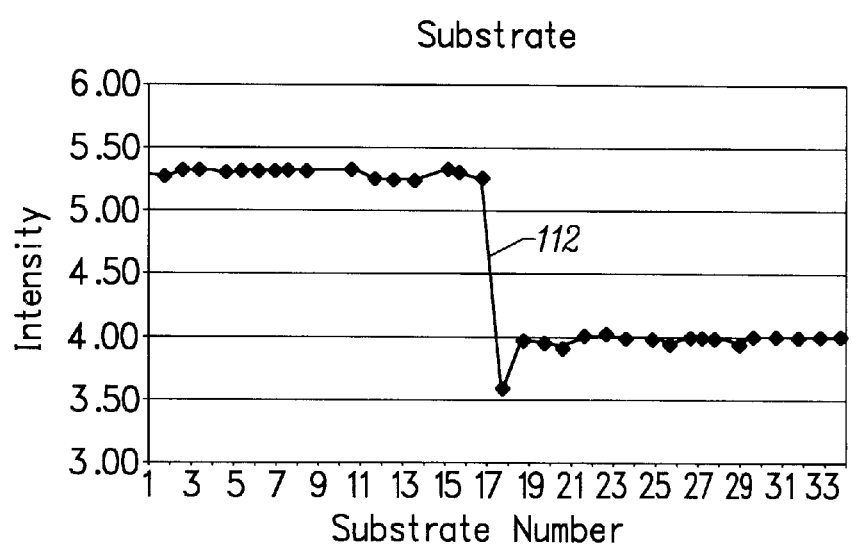
FIG. 4 is a graphical representation of intensity levels of an emission spectral from the plasma generated in the processing chamber, shown above in FIGS. 1–3, for a plurality of baseline substrates in accordance with the present invention.

Referring to FIGS. 1 and 4, the curve 112 shows that there is a substantial drop in the total emission for the 33 substrates processed. Specifically, the curve 112 shows a substantial drop in the total plasma emission for substrate 90. Realizing that the reduction in the plasma emission may result from degradation of the operation of any one or more of the various subsystems associated with the processing system 12, the wavelength dependence of the observed drop in plasma intensity was determined. Specifically, it was round that three different bands of wavelengths carried information corresponding to faults in differing systems. The three differing bands of wavelengths are the ultra-violet (UV) range (250 nm<$\lambda$<400 nm), the "Blue" range (400 nm<$\lambda$<500 nm), and the "Red" range (500 nm<$\lambda$<900 nm). The sub-ranges were chosen based on observed qualitative differences in the spectra for the three regions, discussed below.

Figure 5:
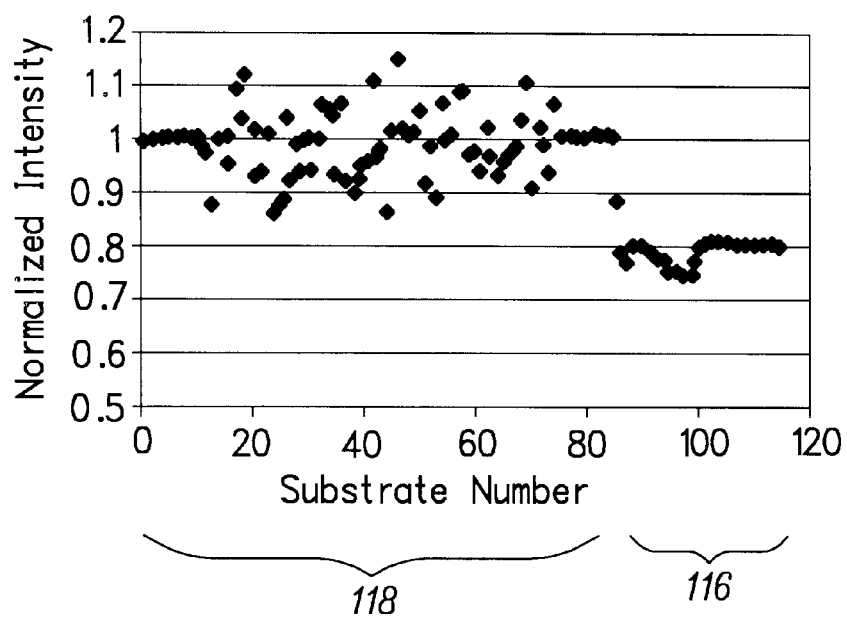
FIG. 5 is a graphical representation of intensity levels of an emission spectra in the range of wavelengths from 500 to 800 nm from the plasma generated in the processing chamber, shown above in FIGS. 1–3, for the plurality of baseline substrates shown above with respect to FIG. 4 for a plurality of test substrates, in accordance with the present invention.
Figure 6:
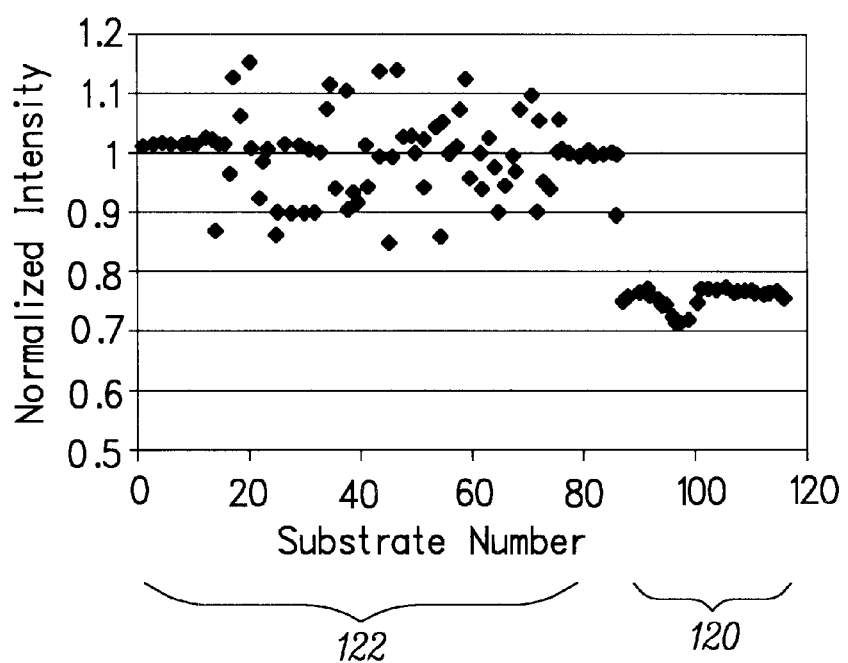
FIG. 6 is a graphical representation of intensity levels of an emission spectra in the range of wavelengths from 400 to 500 nm from the plasma generated in the processing chamber, shown above in FIGS. 1–3, for the plurality of baseline substrates shown above with respect to FIG. 4 and for a plurality of test substrates, in accordance with the present invention.
Figure 7:
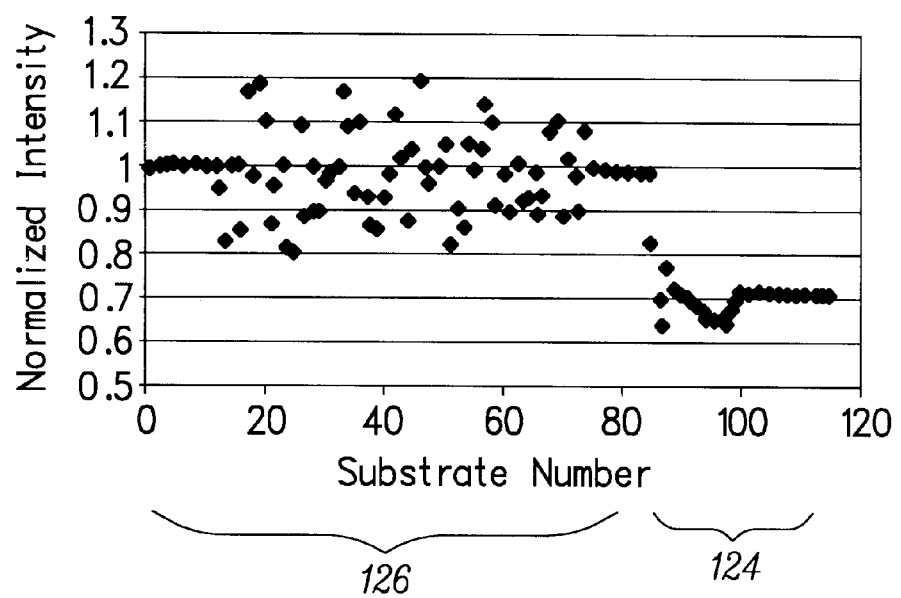
FIG. 7 is a graphical representation of intensity level of an emission spectra in the range of wavelengths from 250 to 400 nm from the plasma generated in the processing chamber, shown above in FIGS. 1–3, for the plurality of baseline substrates shown above with respect to FIG. 4 and for a plurality of test substrates, in accordance with the present invention.

Referring to FIGS. 5, 6 and 7, graphical representations of normalized intensity for various wavelengths of 118 substrates that include the aforementioned 33 baseline substrates, were analyzed during the occurrence of the process fault. In FIG. 5, the intensity of the red wavelength (500 nm<$\lambda$<900 nm) is shown to decrease in region 116, as a result of the fault. Region 116 corresponds to substrates 82 to 118. Specifically, a 20% reduction in the red wavelengths is shown in region 116, compared to region 118. FIG. 6, on the other hand, shows the intensity for the blue wavelengths (400 nm<$\lambda$<500 nm) being reduced approximately 25% in region 120, when compared to region 122. Region 120 also corresponds to substrate 82–118. Finally, FIG. 7 shows the intensity for the UV wavelengths (250 nm<$\lambda$<400 nm) being reduced approximately 30% in region 124, when compared to region 126. Region 120 also corresponds to substrates 82–118. It is believed that the reduction in the intensity of the UV wavelengths may result from either scattering of photons by a film on the window 20, shown in FIG. 1, or degradation of the fiber optic cable 24. The reduction of the red and blue wavelengths may results from absorption of photons by the same. Based upon the foregoing it is assumed that the fault attributable to the reduction in plasma emission between the three spectral bands may be in the optical subsystem.

Figure 8:
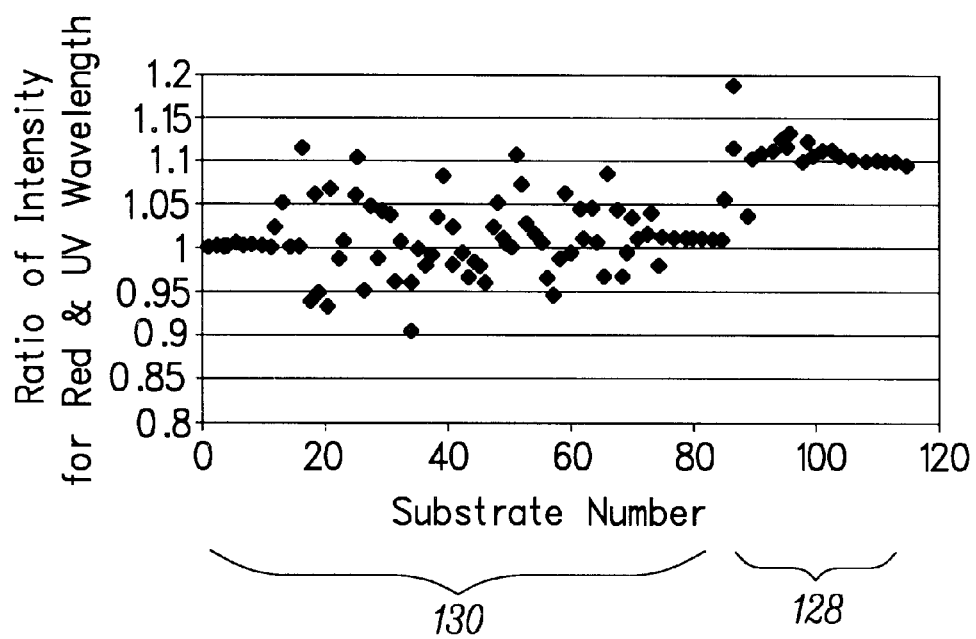
FIG. 8 is a graphical representation of intensity levels of a ratio of the emission shown above in FIG. 5 to the emission spectra shown above in FIG. 7, in accordance with the present invention.

To confirm that the cause for the reduction in plasma intensity resulted from the optics subsystem, a ratio of two of the three aforementioned spectral bands is analyzed. The ratio of red wavelengths to the UV wavelengths is obtained. Specifically, it was found that an increase in the ratio of the red to UV wavelengths indicates that the cause of the fault lies in the optical subsystem. This is shown in FIG. 8 as an increase in the value of the ratios shown in region 128, when compared to region 130. The values of the ratios in region 128 are approximately 10% greater than the value of the ratios in region 130. Therefore, it may be determined that the reduction in plasma emissions is attributable to the optical subsystem.

To distinguish between the components of the optical subsystem that may have caused the fault, the ratios of blue wavelengths to UV wavelengths are obtained. It was found that an increase in ratios of the red to UV wavelengths and an increase in the ratios of the blue to UV wavelengths indicates that the predominate cause of the fault results from the clouding of the window 20. However, were there found to be minor, or none, changes in the ratio of the blue to UV wavelengths while an increase in the ratios of the red to UV wavelengths was present, then the proximate cause of the fault may be attributed to the optical fiber 24.

Figure 9:
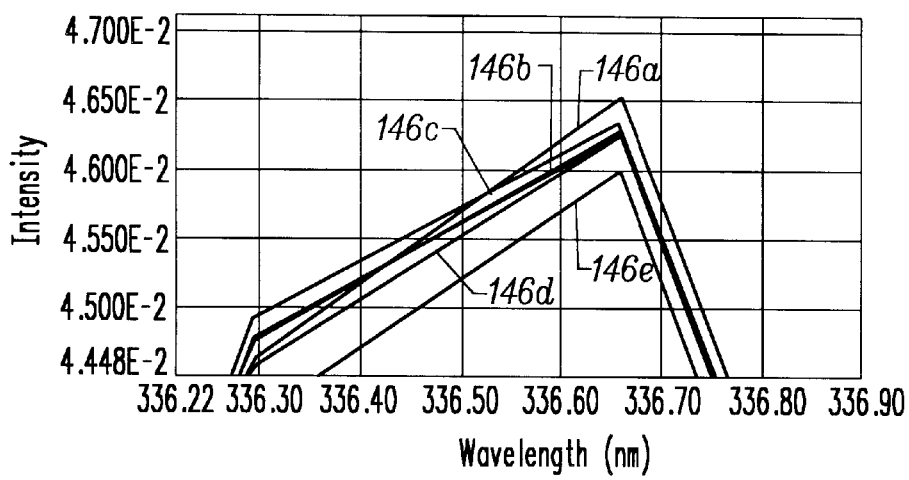
FIG. 9 is a graphical representation showing intensity of emission spectra centered about 336.66 nm of a plurality of emission spectra generated by a plasma in the processing chamber shown above in FIGS. 1–3, with each of the emission spectra corresponding to one of five substrates.
Figure 10:
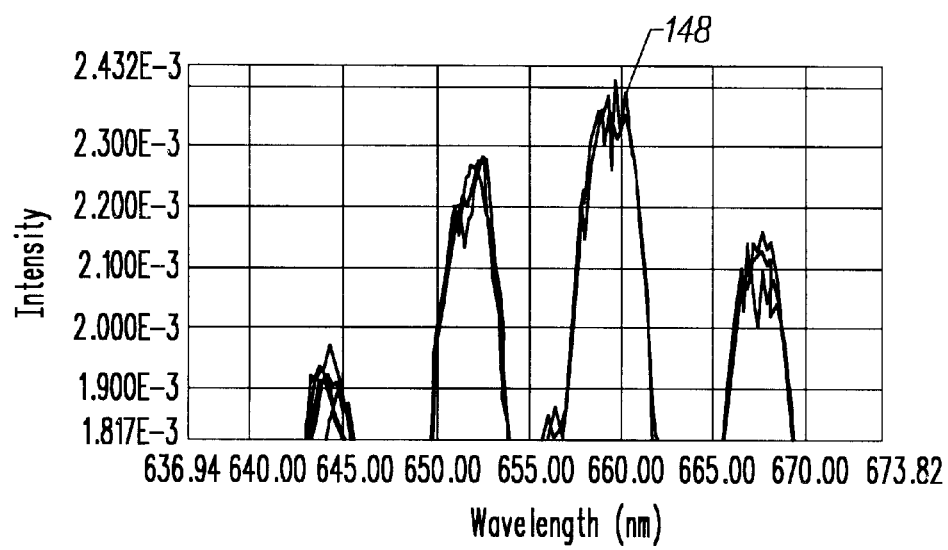
FIG. 10 is a graphical representation showing intensity of emission spectra in the range of 379 to 426 nm demonstrating the five substrates discussed above with respect to FIG. 10.

Referring to FIGS. 1 and 9, another technique to determine that the window 20 is the component of the optical subsystem that is responsible for the decrease in spectroscopic emission fault is determined by analyzing spectra from a plurality of substrates. Specifically, a plurality of substrates was sequentially processed that produced a sequence of spectra of optical energy, shown as 146a, 146b, 146c, 146d and 146e. Each of the spectra 146a, 146b, 146c, 146d and 146e and centered around $\lambda_0$=336.66 nm and has an intensity level associated therewith, with the intensity level in each of the spectra being less than the previous spectra in the sequence. The decrease in intensity is very subtle, however, in that the difference between the first substrate in the sequence, corresponding to curve of spectra 146a, and the last substrate in the sequence, corresponding to curve of spectra 146e, is approximately 1%. This variation in intention among sequentially process substrates is absent, however, in longer wavelengths spectra, shown by curve 148 in FIG. 10. Therefore, this is consistent with UV scattering from a film on the chamber window 20 and is a good indication of a fault that corresponds to inadequate cleaning of the processing chamber 16.

Referring to FIGS. 2, 3 and 9, were a decrease in the value of the ratios of the red to UV wavelengths observed, then the fault may be attributable to other subsystems of the processing system 12. The process parameters controlled by the various subsystems of the processing system 12 were found to have unique spectral signatures by which faults could be identified. For example, the intensity of the range of wavelengths from 410 to 416 nm was found to vary as a function of changes in chamber pressure, spacing of the substrate 90 from the showerhead 54, power supplied by the RF power supply system 30 and the flow rate of silane into the processing chamber 16. Thus, the wavelengths from 410 to 416 nm is considered to be a correlated band of wavelengths for the process parameters associated with chamber pressure, substrate 90 spacing, RF power and silane gas flow.

Were the chamber pressure to increase able a baseline pressure, then the intensity in this range of wavelengths would increase, possibly indicating a high pressure fault. Conversely, were the chamber pressure to decrease below the baseline pressure, then the intensity in this range of wavelengths would decrease, possibly indicating a low pressure fault. Similarly, were the power supplied by the RF power supply system 30 above the baseline power level, then the intensity in this range of wavelengths would increase, and the intensity would decrease were the power level below the baseline power level. In this manner, a power level fault may be indicated.

The correlation between intensity level and silane flow rate into the processing chamber 16 was the inverse of that associated with the chamber pressure and the power level. Specifically, were the silane flow rate into the processing chamber 16 above the baseline flow rate, then the intensity in this range of wavelengths would decrease. An increase in the intensity level for this range of wavelengths is observed when the silane flow rate is below the baseline flow rate. In this manner, a silane flow rate fault may be indicated.

When the spacing between the substrate 90 and the showerhead 54 was too great, this resulted in an increase in the intensity of wavelengths in the range of 410–416 nm, possibly indicating a spacing too great fault. When the substrate 90 was too close to the showerhead 54 there was no detectable change in the intensity level in this range of wavelengths.

Distinguishing between the differing subsystems that might be the source of the aforementioned faults may be achieved by identifying spectral bands that do not correlate with the process parameter of interest. Specifically, a parameter disjunctive band is identified in which intensity does not vary in response to the presence of the fault of interest, but varies in accordance with the remaining faults associated with the correlated band. Also identified is a globally disjunctive band. The globally disjunctive band of wavelengths has intensities associated therewith that do not vary in response to the presence of any of the aforementioned faults. The globally disjunctive band of wavelengths is in the range of 460 to 488 nm. From aforementioned bands, two ratios are obtained. A parameter ratio is obtained by taking the ratio of the correlated band to the distinctive band. A normalized ratio is obtained by taking the ratio of the correlated band to the globally disjunctive band. Were the parameter ratio and the normalized ratio found to match, then the subsystem that controlled the process parameter associated with the parameter disjunctive band would be identified as the cause of the fault. Were the two ratios found not to match, it may be assumed that the fault was associated with the subsystems that correspond to one of the remaining process parameters.

In the present example, the parameter disjunctive band for the chamber pressure was found to consist of wavelengths in the range of 416–421 nm. To determine whether the variance in the correlated band of wavelengths in the range of 410–416 nm corresponded to the chamber pressure parameter, the parameter ratio would be obtained. To that end, a ratio of the correlated band, having wavelengths in the range of 410–416 nm, to the parameter disjunctive band, having wavelengths in the range of 416–421 nm, would be obtained. This ratio would be compared to the normalized ratio. The normalized ratio would be determined by taking a ratio of the correlated band, having wavelengths in the range of 410–416 nm, to the globally disjunctive band, having wavelengths in the range of 460–488 nm. Were the two aforementioned ratios found to match, then it could be highly indicative that an increase in the intensity of the correlated band identified the chamber pressure as being greater than a baseline pressure. Conversely, a decrease in the intensity level of the correlated band identifies the chamber pressure as being below a baseline pressurization. Thus, the subsystem that controlled the chamber pressure would be identified as a cause of the fault.

Were the two aforementioned ratios found not to match, then another parameter disjunctive band would be analyzed, which correspond to a differing parameter. By way of example, the parameter disjunctive band corresponding to power level supplied by the RF power supply 30 is analyzed. The parameter disjunctive band corresponding to the power level was found to be in the range of wavelengths of 395–401.5 nm. As discussed above, a parameter ratio and a normalized ratio would be determined and compared. A match between the two ratios would indicate that an increase in the intensity of the correlated band showed that the power level is greater than a baseline pressure. Conversely, a decrease in the intensity level of the correlated band identifies the power level as being below a baseline power level. This would indicate that the subsystem that controlled the RF power was the cause of the fault.

Were a match not found, then another process parameter would be analyzed in the similar manner. To the end, the parameter disjunctive band associated with the silane flow rate could be analyzed. The disjunctive band associated with the silane flow rate was found to include wavelengths in the range of 386–392.5 nm.

A correlated band for the nitrous oxide parameter was found to be in range of wavelengths of 372.5–376.8 nm, which also correlated to the chamber pressurization and spacing process parameters. Specifically, were the flow rate of the nitrous oxide to increase above a baseline flow rate, then the intensity in the range of wavelengths of 372.5–376.8 nm would increase. Conversely, were the flow rate of the nitrous oxide to decrease below a baseline flow rate, then the intensity in the range of wavelengths of 372.5–376.8 nm would decrease. The change in the intensity level for the chamber pressurization was inversely proportional to the change in chamber pressurization. When the spacing between the substrate 90 and the showerhead 54 was too great, this also resulted in an increase in the intensity of wavelengths in the range of 372.5–376.8 nm. When the substrate 90 was too close to the showerhead 54 there was no detectable change in the intensity level in this range of wavelengths.

The parameter disjunctive band for the flow rate of nitrous oxide was found to be in the range of wavelengths of 392.5–395.0 nm. Employing the process described above, one could determine whether the fault may be identified as being with the flow rate of the nitrous oxide process parameter.

In the most direct manner, the process faults may be detected and classified employing a look-up table in memory 38, shown in FIG. 2, in which information corresponding to the aforementioned spectral signatures to the faults is stored. To that end, the memory 38 would include information concerning wavelength, intensity and temporal characteristics of the optical energy associated with the faults that may be determined empirically.

Figure 11:
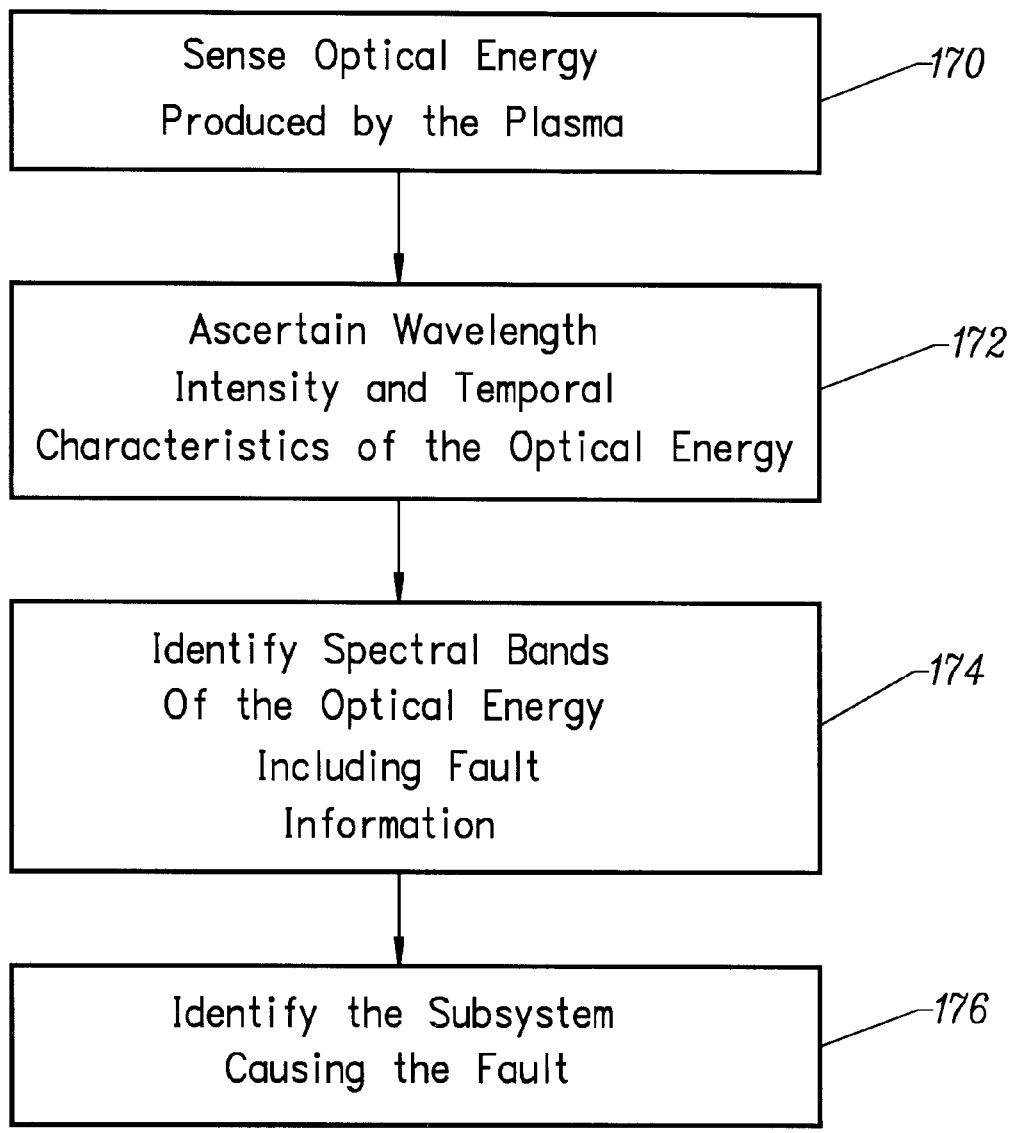
FIG. 11 is a flow chart showing the steps of the method for measuring film characteristics as a function of the wavelength and intensity of optical energy, in accordance with the present invention.

Referring to FIGS. 1, 2 and 11, during operation, optical energy produced by the plasma 100 would be sensed by the spectrum analyzer 22 at step 170 and a signal would be generated in response thereto. The processor 36 would operate on the signal to quantize, e.g. digitize the same and ascertain the wavelength, intensity and temporal characteristics of the optical energy sensed by the spectrum analyzer 22 at step 172. At step 174, the processor 36 would identify spectral bands from the wavelengths that contain information corresponding to one of the aforementioned faults. To that end, the processor 36 would operate on data entries in the memory 38 to find a data entry having spectral information that matches the spectral information sensed by the spectrum analyzer 22, defining matched data. This may be achieved by finding an exact correspondence or through an interpolative process to determine the data entry that is the closest match to the sensed optical energy. Were a corresponding data entry ascertained, the fault in the process may be determined, and, if possible, the subsystem that caused the fault may be identified at step 176. If no subsystem may be identified, then the system 12 may be identified as being in need of calibration.

As discussed above with respect to FIG. 2, the processor 36 controls the operation of the PECVD system. This is achieved by having the processor 36 operate on system control software that is stored in a memory 38. The computer program includes sets of instructions that dictate the timing, mixing of fluids, chamber pressure, chamber temperature, RF power levels, and other parameters of a particular process, discussed more fully below. The memory 38 may be any kind of memory, such as a hard disk drive, floppy disk drive, random access memory, read-only-memory, card rack or any combination thereof. The processor 36 may contain a single-board computer (SBC), analog and digital input/output boards, interface boards and stepper motor controller boards that may conform to the Versa Modular European (VME) standard that defines board, card cage, and connector dimensions and types. The VME standard also defines the bus structure as having a 16-bit data bus and a 24 -bit address bit.

Figure 12:
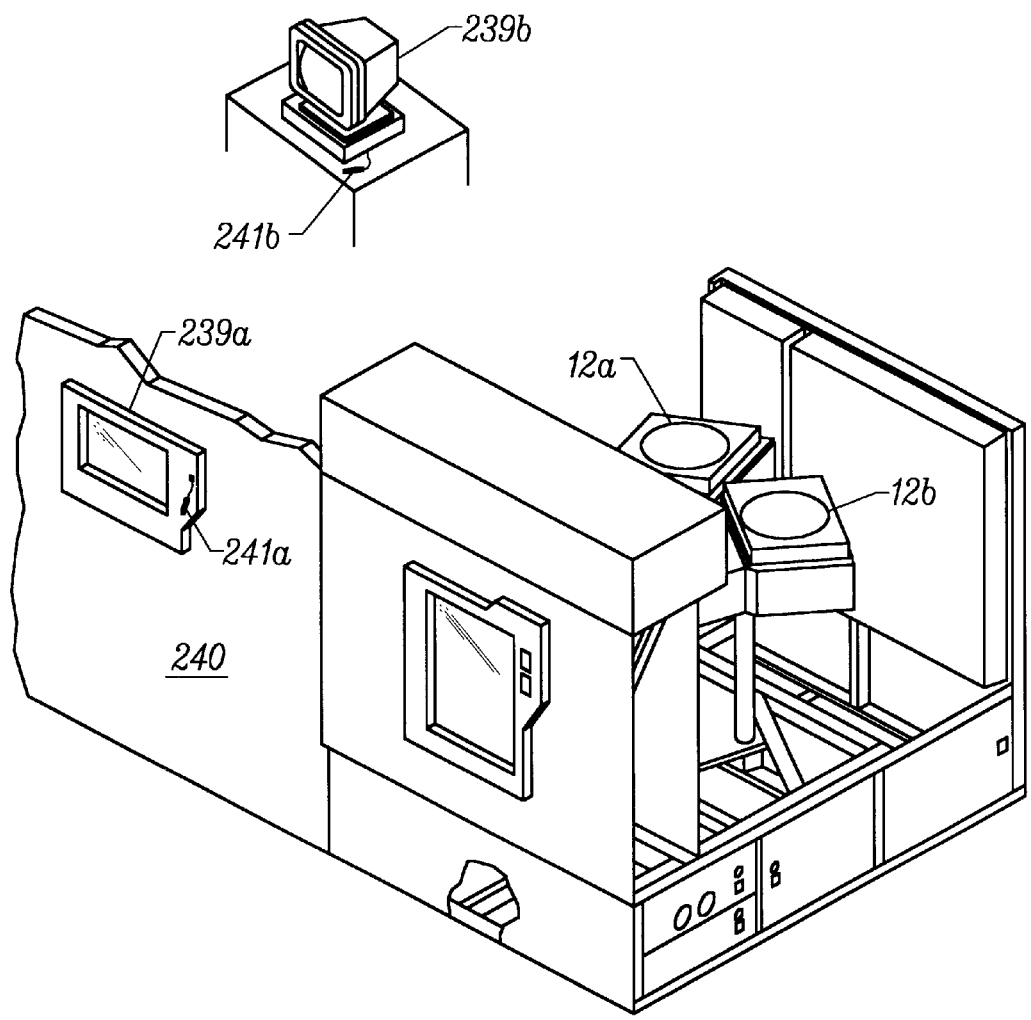
FIG. 12 is a perspective view of a processing environment in which the processing chambers, shown above in FIGS. 1–3, may be employed.

Referring to both FIGS. 2 and 12, the interface between a user and the processor 36 may be via a visual display. To that end, two monitors 239a and 239b may be employed. One monitor 239a may be mounted on a clean room wall 240 having one or more PECVD systems 12a and 12b. The remaining monitor 239b may be mounted behind the wall 240 for service personnel. The monitors 239a and 239b may simultaneously display the same information. Communication with the processor 36 may be achieved with a light pen associated with each of the monitors 239a and 239b. For example, light pen 241a facilitates communication with the processor 36 through monitor 239a, and light pen 241b facilities communication with the processor 36 through monitor 239b. A light sensor in the tip of the light pens 241a and 241b detects light emitted by CRT display in response to a user pointing the same to an area of the display screen. The touched area changes color, or a new menu or screen is displayed, confirming communication between the light pen and the display screen. Other devices, such as a keyboard, mouse, or other pointing or communication devices, may be used instead of or in addition to the light pens 214a and 241b to allow the user to communicate with the processor 36.

As discussed above, the computer program includes sets of instructions that dictate the timing, mixture of fluids, chamber pressure, chamber temperature, RF power levels, and other parameters of a particular process, as well as analyzing the information obtained by the spectrum analyzer 22, discussed more fully below. The computer program code may be written in any conventional computer readable programming language; for example, 68000 assembly language, C, C++, Pascal, Fortan and the like. Suitable program code is entered into a single file, or multiple files, using a conventional text editor and stored or embodied in a computer-readable medium, such as a memory system of the computer. If the entered code text is in a high level language, the code is compiled, and the resultant compiler code is then linked with an object code of precompiled Windows® library routines. To execute the linked and compiled object code the system user invokes the object code, causing the computer system to load the code in memory. The processor 36 then reads and executes the code to perform the tasks identified in the program.

Figure 13:
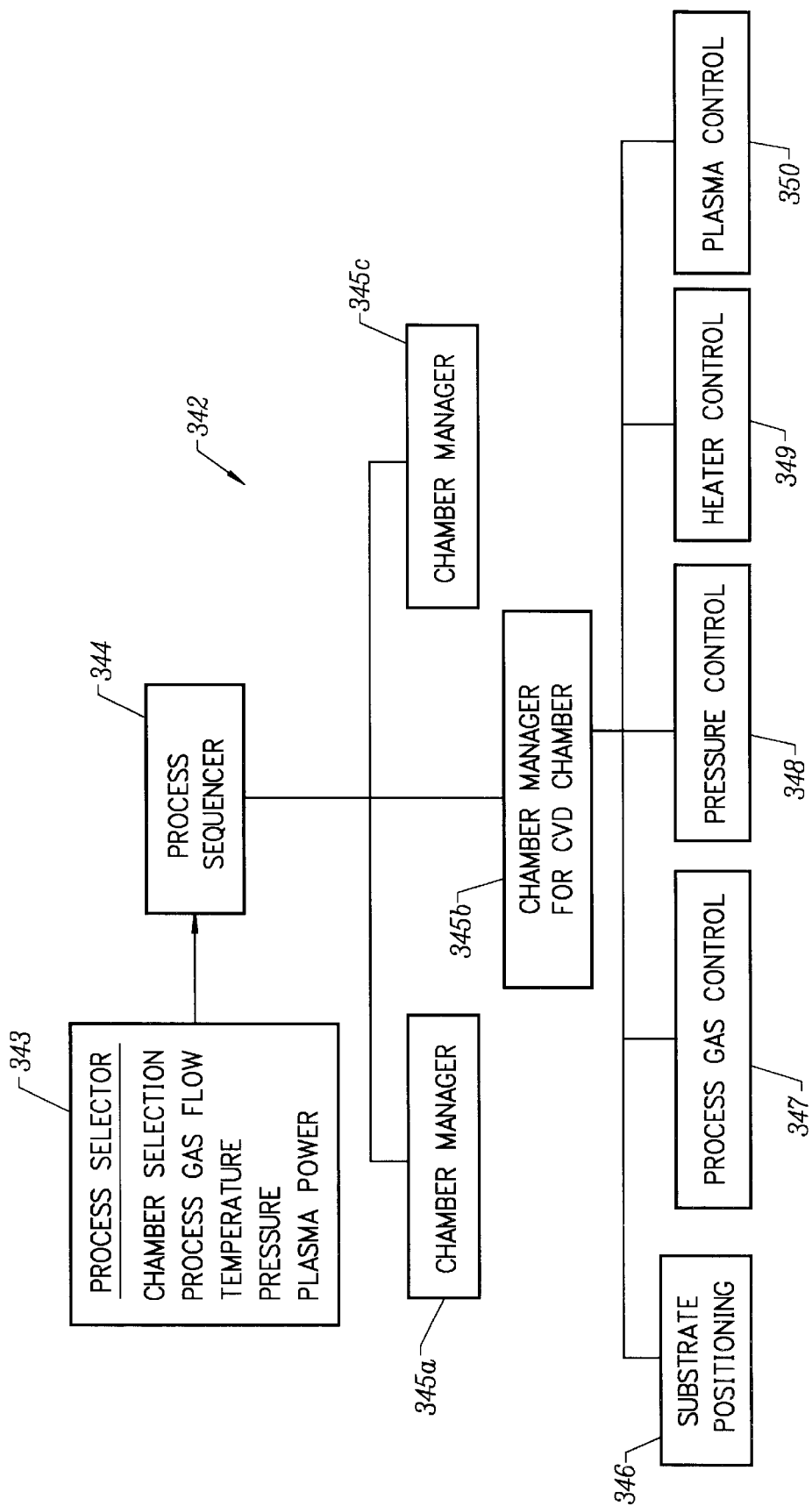
FIG. 13 is a block diagram showing the hierarchical control structure of system control software employed to control the processing system, shown above in FIG. 2.

Referring to FIG. 13, an illustrative block diagram of the hierarchical control structure of the system control software, computer program 342, according to a specific embodiment is shown. Using a light pen interface, a user enters a process set number and process chamber number into a process selector subroutine 343 in response to menus or screens displayed on the CRT monitor. The process sets, which are predetermined sets of process parameters necessary to carry out specified processes, are identified by predefined set numbers. Process selector subroutine 343 identifies (i) the desired process chamber, and (ii) the desired set of process parameters needed to operate the process chamber for performing the desired process. The process parameters for performing a specific process relate to process conditions such as, for example, process gas composition and flow rates, temperature pressure, plasma conditions such as high- and low-frequency RF power levels and the high-frequency and low-frequency RF frequencies, (and in addition, microwave generator power levels for embodiments equipped with remote microwave plasma systems) cooling gas pressure, and chamber wall temperature. Process selector subroutine 343 controls what type of process deposition; wafer cleaning, chamber cleaning, chamber gettering, reflowing) is performed at an appropriate time. In some embodiments, there may be more than one process selector subroutine.

A process sequencer subroutine 344 comprises program code for accepting the identified process chamber and set of process parameters from process selector subroutine 343, and for controlling operation of the various process chambers. Multiple users can enter process set numbers and process chambers number, or a single user can enter multiple process set numbers and process chamber numbers, so sequencer subroutine 344 operates to schedule the selected processes in the desired sequence. Preferably, sequencer subroutine 344 includes program code to perform the steps of (i) monitoring the operation of the process chamber to determine if the chambers are being used, (ii) determining what processes are being carried out in the processing chambers being used, and (iii) executing the desired process based on availability of a process chamber and the type or process to be carried out. Conventional methods of monitoring the processing chambers can be used, such as polling. When scheduling the process to be executed, sequencer, subroutine 344 may be designed to take into consideration the present condition of the processing chamber being used in comparison with the desired process conditions for a selected process, or the "age" of each particular user-entered request, or any other relevant factor a system programmer desires to include for determining scheduling priorities.

Once sequencer subroutine 344 determines which processing chamber and process set combination is going to be executed next, the sequencer subroutine 344 initiates execution of the process set by passing the particular process set parameters to a chamber manager subroutine 345a–c that controls multiple processing tasks according to the process set determined by sequencer subroutine 344. For example, the chamber manager subroutine 345b comprises program code for controlling operations in processing chamber 16, shown in FIG. 3. Chamber manager subroutine 345b also controls execution of various chamber component subroutines which control operation of the chamber components necessary to carry out the selected process set. Examples of chamber component subroutines are substrate positioning subroutine 346, process gas control subroutine 347, pressure control subroutine 348, heater control subroutine 349, and plasma control subroutine 350. Depending on the specific configuration of the system chamber, some embodiments include all of the above subroutines, while other embodiments may include only some of the subroutines. Those having ordinary skill in the art would readily recognize that other chamber control subroutines can be included depending on what processes are to be performed in the processing chamber 16. In operation, chamber manager subroutine 345b selectively schedules or calls the process component subroutines in accordance with the particular process set being executed. Chamber manager subroutine 345b schedules the process component subroutines much like process sequencer subroutine 344 schedules which processing chamber 16 and process set is to be executed next. Typically, chamber manager subroutine 345b includes steps of monitoring the various chamber components, determining which components need to be operated based on the process parameters for the process set to be executed, and initiating execution of a chamber component subroutine responsive to the monitoring and determining steps.

Referring to both FIGS. 3 and 13, the substrate positioning subroutine 346 comprises program code for controlling chamber components that are used to load the substrate 90 onto pedestal 86 and, optionally, to lift the substrate 90 to a desired height in processing chamber 16 to control the spacing between the substrate 90 and showerhead 54. When a substrate 90 is loaded into processing chamber 16, pedestal 86 is lowered to receive the substrate 90 in wafer pocket 88, and then is raised to the desired height. In operation, substrate positioning subroutine 346 controls movement of pedestal 86 in response to process set parameters related to the support height that are transferred from chamber manager subroutine 345b.

Process gas control subroutine 347 has program code for controlling process gas composition and flow rates. Process gas control subroutine 347 controls the open/close position of the safety shut-off valves (not shown), and also ramps up/down the mass flow controllers (not shown) to obtain the desired gas flow rate. Process gas control subroutine 347 is invoked by the chamber manager subroutine 345b, as are all chamber component subroutines, and receives subroutine process parameters related to the desired gas flow rates from the chamber manager. Typically, process gas control subroutine 347 operates by opening the gas supply lines and repeatedly (i) reading the necessary mass flow controllers, (ii) comparing the readings to the desired flow rates received from chamber manager subroutine 345b, and (iii) adjusting the flow rates of the gas supply lines as necessary. Furthermore, process gas control subroutine 347 include steps for monitoring the gas flow rates for unsafe rates, and activating the safety shut-off valves (not shown) when an unsafe condition is detected. Process gates control subroutine 347 also controls the gas composition and flow rates for clean gases as well as for deposition gases, depending on the desired process (clean or deposition or other) that is selected. Alternative embodiments, could have more than one process gas control subroutine, each subroutine controlling a specific type of process or specific sets of gas lines.

In some processes, an inert gas such as nitrogen, $N_2$, or argon, Ar, is flowed into processing chamber 16 to stabilize the pressure in the chamber before reactive process gases are introduced. For these processes, process gas control subroutine 347 is programmed to include steps for flowing the inert gas into processing chamber 16 for an amount of time necessary to stabilize the pressure in the chamber, and then the steps described above would be carried out. Additionally, when a process gas is to be vaporized from a liquid precursor, for example $TiCl_4$, process gas control subroutine 347 would be written to include steps for bubbling a delivery gas, such as helium, through the liquid precursor in a bubbler assembly (not shown), or for introducing a carrier gas, such as helium, to a liquid injection system. When a bubbler is used for this type of process, process gas control subroutine 347 regulates the flow of the delivery gas, the pressure in the bubbler (not shown), and the bubbler temperature in order to obtain the desired process gas flow rates. As discussed above, the desired process gas flow rates are transferred to process gas control subroutine 347 as process parameters. Furthermore, process gas control subroutine 347 includes steps for obtaining the necessary delivery gas flow rate, bubbler pressure, and bubbler temperature for the desired process gas flow rate by accessing a stored table containing the necessary values for a given process gas flow rate. Once the necessary values are obtained, the delivery gas flow rate, bubbler pressure and bubbler temperature are monitored, compared to the necessary values and adjusted accordingly.

The pressure control subroutine 348 comprises program code for controlling the pressure in the processing chamber 16 by regulating the aperture size of the throttle valve in the exhaust system of the chamber. The aperture size of the throttle valve 84 is set to control the chamber pressure at a desired level in relation to the total process gas flow, the size of the processing chamber 16, and the pumping set-point pressure for the exhaust system. When pressure control subroutine 348 is invoked, the desired or target pressure level is received as a parameter from chamber manager subroutine 345b. The pressure control subroutine 348 measures the pressure in the processing chamber 16 by reading one or more conventional pressure manometers connected to the chamber, compares the measure value(s) to the target pressure, obtains PID (proportional, integral, and differential) values corresponding to the target pressure from a stored pressure table, and adjusts the throttle valve 84 according to the PID values obtained from the pressure table. Alternatively, pressure control subroutine 348 can be written to open or close the throttle valve 84 to a particular aperture size to regulate the pumping capacity in the processing chamber 16 to the desired level.

Heater control subroutine 349 comprises program code for controlling the temperature of a heater element 107 used to resistively heat pedestal 86 (and any substrate thereon). The heater control subroutine 349 is also invoked by the chamber manager subroutine 345b and receives a target, or set-point, temperature parameter. The heater control subroutine 349 measures the temperatures by measuring voltage output of a thermocouple located in pedestal 86, comparing the measured temperature to the set-point temperature, and increasing or decreasing current applied to the heating unit to obtain the set-point temperature. The temperature is obtained from the measured voltage by looking up the corresponding temperature in a stored conversion table, or by calculating the temperature using a fourth-order polynomial. When an embedded loop is used to heat pedestal 86, heater control subroutine 349 gradually controls a ramp up/down of current applied to the loop. Additionally, a built-in fail-safe mode can be included to detect process safety compliance, and can shut down operation of the heating unit if the processing chamber 16 is not properly set up. An alternative method of heater control which may be used utilizes a ramp control algorithm, which is described in the U.S. Pat. No. 5,968,587 to Jonathan Frankel, entitled "Systems and Methods for Controlling the Temperature of a Vapor Deposition Apparatus," and assigned to the assignee of the present invention.

A plasma control subroutine 350 comprises program code for setting low- and high-frequency RF power levels applied to the process electrodes in the processing chamber 16 and pedestal 86, and for setting the low and high RF frequency employed. Like the previously described chamber component subroutines, plasma control subroutine 350 is invoked by chamber manager subroutine 345b. For embodiments including remote a plasma generator, the plasma control subroutine 350 would also include program code for controlling the remote plasma generator.

Although the invention has been described in terms of specific embodiments, one skilled in the art will recognize that various wavelengths may be sensed to detect the faults identified above, or additional faults. In addition, the present invention may be employed to dynamically control process conditions in response to the spectra sensed by the spectra analyzer via feedback control. Therefore, the scope of the invention should not be based upon the foregoing description. Rather, the scope of the invention should be determined based upon the claims recited herein, including the full scope of equivalents thereof.

What is claimed is:

1. A method for detecting one of a plurality of faults in processing conditions of a semiconductor processing system employing a plasma, said method comprising:

sensing optical energy produced by said plasma, said optical energy having a plurality of spectral bands associated therewith;

identifying a first subset of said plurality of spectral bands that has a first intensity associated therewith that varies in response to said plurality of faults, and a second subset of said plurality of spectral bands that has a second intensity associated therewith that varies substantially independently of the presence of said one of said plurality of faults and a third subset of spectral bands having a third intensity associated therewith that varies substantially independently of said plurality of faults; and detecting said one of said plurality of faults as a function of said first, second and third subsets.

2. The method as recited in claim 1 wherein detecting further includes ascertaining said one of said plurality of faults as a function of a ratio of said first and second subsets.

3. The method as recited in claim 1 wherein detecting said one of said plurality of faults further includes quantizing said first, second and third subsets, defining first, second and third quantizations and obtaining a ratio of said first and second quantizations, defining a parameter ratio, and obtaining a ratio of said first and third quantizations, defining a normalized ratio and ascertaining said one of said plurality of faults based upon a match between said parameter ratio and said normalized ratio.

4. The method as recited in claim 1 further including exposing a plurality of substrates, sequentially, to said plasma, producing a sequence of emissions of said optical energy, with each of said emissions of said sequence including said first, second and third subsets that have intensity levels associated therewith that correspond to one of said plurality of substrates, wherein detecting further includes identifying said one of said plurality of faults as a function of variations among the intensity levels of said emissions of said sequence.

5. The method as recited in claim 2 further including exposing a plurality of substrates, sequentially, to said plasma, producing a sequence of said ratio, with each ratio in said sequence corresponding to one of said plurality of substrates and having a value associated therewith, with the values of the ratios of said sequence defining a set of values, wherein detecting further includes identifying said one of said plurality of faults as a function of variations in said set of values.

6. The method as recited in claim 1 wherein determining said one of said plurality of faults further includes quantizing said first, second and third subsets, defining first, second and third quantizations and obtaining a ratio of said first and second quantizations, defining a parameter ratio, and obtaining a ratio of said first and third quantizations, defining a normalized ratio and ascertaining said fault based upon a comparison between said parameter ratio and said normalized ratio.

7. A method for detecting one of a plurality of processing conditions of a semiconductor processing system employing a plasma, said method comprising:

providing said semiconductor processing system with a plurality of subsystems;

sensing optical energy produced by said plasma, said optical energy having a plurality of spectral bands associated therewith;

identifying first, second and third subsets of said plurality of spectral bands, with said first subset having a first intensity associated therewith that varies in response to said one of said plurality of processing conditions, said second subset having a second intensity associated therewith that varies substantially independently of the presence of said one of said plurality of processing conditions, and said third subset having a third intensity associated therewith that varies substantially independently of substantially all of said plurality of processing conditions; and detecting said one of said plurality of processing conditions as a function of said first, second and third subsets.

8. The method as recited in claim 2 wherein detecting said one of said plurality of processing conditions further includes quantizing said first and second intensities, defining first and second quantizations and obtaining a ratio of said first and second quantizations.

9. The method as recited in claim 7 further including quantizing said first, second and third subsets, defining first, second and third quantizations, respectively, and obtaining a ratio of said first and second quantizations, and obtaining a ratio of said first and third quantizations, defining a normalized ratio, with said ratio of said first and second quantizations defining a parameter ratio, with detecting said one of said plurality of processing conditions further including correlating said one of said plurality of processing conditions to said one of said plurality of subsystems based upon a match between said parameter ratio and said normalized ratio.

10. The method as recited in claim 9 further including exposing a plurality of substrates, sequentially, to said plasma, producing a sequence of said ratio, with each ratio of said sequence corresponding to one of said plurality of substrates and having a value associated therewith, with the values of the ratios of said sequence defining a set of values, wherein detecting said one of said plurality of processing conditions further includes identifying said one of said plurality of processing conditions as a function of variations in said set of values.

11. The method as recited in claim 8 wherein quantizing further includes quantizing said third subset, wherein first, second and third quantizations are defined from quantizing said first, second and third subsets, and obtaining a ratio of said first and second quantizations, further includes obtaining a ratio of said first and third quantizations, defining a normalized ratio, with said ratio of said first and second quantizations defining a parameter ratio, with determining said one of said plurality of processing conditions further including ascertaining said one of said plurality of processing conditions based upon a comparison between said parameter and said normalized ratio.

12. An apparatus for characterizing processing conditions of a semiconductor processing system employing a source of light in a processing chamber, said apparatus comprising:

a detector in optical communication with said processing chamber to sense optical energy generated by said source of light, said optical energy having a plurality of spectral bands associated therewith;

a spectral analyzer, in electrical communication with said optical detector, to resolve said spectral bands and produce information corresponding thereto;

a processor in electrical communication with said spectrum analyzer; and a memory in electrical communication with said processor, said memory comprising a computer-readable medium having a computer-readable program embodied therein, said computer-readable program including a set of instructions to cause said processor to operate on said information to identify a first subset of said plurality of spectral bands that has a first intensity associated therewith that varies in response to one of said processing conditions, and a second subset of said plurality of spectral bands that has a second intensity associated therewith that varies substantially independently of said one of said processing conditions and a second set of instructions to cause said processor to operate on said information to identify a third subset of spectral bands having an intensity associated therewith that varies substantially independently of said processing conditions and a third set of instructions to cause said processor to characterize said one of said processing conditions as a function of said first, second and third intensities.

13. The apparatus as recited in claim 12 wherein said computer-readable program further includes a subroutine to quantize said first and second intensities, defining first and second quantizations and obtain a ratio of said first and second quantizations.

14. The apparatus as recited in claim 13 wherein said computer-readable program further includes a supplementary set of instructions to produce a plurality of said ratios, defining a sequence, with each of the ratios in said sequence corresponding to one of a plurality of substrates, sequentially exposed to said source of light, with said third set of instructions further including a subroutine to characterize said one of said processing conditions as a function of variations among the ratios of said sequence.

15. The apparatus as recited in claim 12 wherein said third set of instructions further includes a subroutine to characterize said one of said processing conditions as being in one of two states selected from a set of states consisting of a fault state and an acceptable operation state.

16. The apparatus as recited in claim 12 wherein said source of light further includes a system to produce a plasma within said processing chamber.

17. A method for monitoring processing conditions of a semiconductor processing system employing a source of light, said method comprising:

sensing optical energy produced by said source of light, said optical energy having a plurality of spectral bands associated therewith;

ascertaining a first subset of said plurality of spectral bands having first and second sets of frequencies associated therewith, with said first and second sets of frequencies having an intensity associated therewith, defining first and second intensities, respectively, with said first intensity varying a first magnitude in response to changes in multiple processing conditions and said second intensity varying a second magnitude in response to said multiple processing conditions, with said second magnitude being less than said first magnitude;

identifying a second subset of said spectral bands having an intensity associated therewith that varies a third magnitude in response to changes in a subset of said multiple processing conditions, with said third magnitude being less than said first and second magnitudes;

obtaining a first ratio of intensities of said second subset and said first set of frequencies;

obtaining a second ratio of said second subset and said second set of frequencies; and determining a state of one of said multiple processing conditions by comparing said first and second ratios.

18. The method as recited in claim 17 wherein said state is selected from a set of states consisting essentially of a fault state and an acceptable operation state.

19. The method as recited in claim 17 further including providing said processing system with a plurality of subsystems wherein said processing conditions include operational characteristics of said subsystems.

20. The method as recited in claim 17 further including quantizing said first and second ratios, with said first ratio defining a normalized ratio and said second ratio defining a parameter ratio, with determining further including determining said state based upon a comparison between said parameter ratio and said normalized ratio.

21. The method as recited in claim 17 further including providing said processing system with a plurality of subsystems wherein said one of said processing conditions include optional characteristics of one of said plurality of subsystems, with said one of said plurality of subsystems selected from a set of subsystems consisting of a power source for said source of light, a light transmissive body in optical communication with said processing chamber, an optical fiber in optical communication with said light transmissive body, a pump system in fluid communication with said processing chamber, lifting system disposed in said processing chamber to support a substrate and a fluid delivery system to deliver processing fluids to said processing chamber.

* * * * *